United States Patent [19]

Prasad et al.

[11] 3,931,401
[45] Jan. 6, 1976

[54] 1,N⁶-ETHENO-5'-ADENOSINE CARBOXAMIDES FOR INCREASING CORONARY SINUS PARTIAL PRESSURE OF OXYGEN

[75] Inventors: Raj Nandan Prasad, Pierrefonds; David Lyon Garmaise, Montreal, both of Canada

[73] Assignee: Abbott Laboratories, North Chicago, Ill.

[22] Filed: May 21, 1974

[21] Appl. No.: 472,029

Related U.S. Application Data

[62] Division of Ser. No. 317,326, Oct. 21, 1972, Pat. No. 3,830,796.

[52] U.S. Cl. .................................................. 424/180
[51] Int. Cl.² ............................................. A61K 31/70
[58] Field of Search ..................................... 424/180

[56] References Cited
UNITED STATES PATENTS

| | | | |
|---|---|---|---|
| 3,551,409 | 12/1970 | Kampe et al. | 260/211.5 R |
| 3,697,504 | 10/1972 | Schmidt | 260/211.5 R |

*Primary Examiner*—Jerome D. Goldberg
*Attorney, Agent, or Firm*—Robert L. Niblack; Vincent A. Mallare

[57] ABSTRACT

Amides of 1,N⁶-Etheno-5'-adensine carboxylic acid represented by the formula

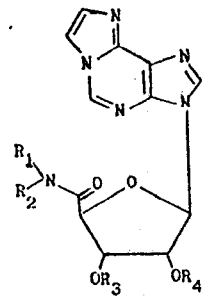

wherein $R_1$ and $R_2$ each are hydrogen, loweralkyl, loweralkenyl, loweralkynyl or cycloalkyl, and $R_3$ and $R_4$ each are hydrogen, acyl, or $R_3$ and $R_4$ taken together form an isopropylidene or benzylidene moiety; and the pharmaceutically acceptable acid addition salts thereof.

The compounds wherein $R_3$ and $R_4$ are hydrogen are useful in treating cardiovascular disorders and are particularly useful as anti-anginal and anti-hypertensive agents. Compounds wherein $R_3$ and $R_4$ are acyl or when taken together form an isopropylidene or benzylidene moiety are intermediates useful in the preparation of the final products. ($R_3$ and $R_4$ = hydrogen).

2 Claims, No Drawings

1,N⁶-ETHENO-5'-ADENOSINE CARBOXAMIDES FOR INCREASING CORONARY SINUS PARTIAL PRESSURE OF OXYGEN

This is a division of application Ser. No. 317,326 filed Oct. 21, 1972, now U.S. Pat. No. 3,830,796 issued Aug. 20, 1974.

DETAILED DESCRIPTION OF THE INVENTION

The present invention relates to adenosine derivatives, to therapeutic compositions containing such derivatives, to methods of preparing and using the novel compounds and to intermediates useful in the preparation of such compounds.

The compounds of this invention are represented by the formula

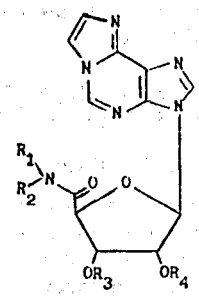

wherein $R_1$ and $R_2$ each are hydrogen, loweralkyl, loweralkenyl, loweralkynyl or cycloalkyl, and $R_3$ and $R_4$ each are hydrogen, acyl, or $R_3$ and $R_4$ taken together form an isopropylidene or benzylidene moiety; and the pharmaceutically acceptable acid addition salts thereof.

The term "loweralkyl" as used herein, refers to both straight and branched chain alkyl radicals containing from 1 to 6 carbon atoms, including methyl, ethyl, n-propyl, iso-propyl, n-butyl, sec-butyl, tert-butyl, iso-butyl, n-pentyl, iso-pentyl, neo-pentyl, n-hexyl and the like.

"Loweralkenyl" refers to the $C_2$ and $C_5$ alkyl groups, as defined above, from which a hydrogen atom has been removed from each of two adjacent carbon atoms to produce ethylenic unsaturation; e.g., vinyl, allyl, methallyl, 1-pentenyl and the like.

"Loweralkynyl" refers to the $C_2$ to $C_5$ alkyl groups as defined above, from which 2 hydrogen atoms have been removed from each of two adjacent carbon atoms to produce acetylenic unsaturation such as ethynyl, propargyl, 2-butynyl, 1-pentynyl and the like.

The term "cycloalkyl" refers to $C_3$ and $C_6$ cycloalkyl groups, namely, cyclopropyl, cyclobutyl, cyclopentyl and cyclohexyl.

The term "pharmaceutically acceptable acid addition salts" refers to non-toxic salts prepared by reacting the amide with the appropriate organic or inorganic acid, or by utilizing an acid addition salt of the appropriate intermediate. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like.

The term "acyl" refers to acetyl, propionyl, butyryl and the like.

The compounds of this invention are useful as antianginal agents at dosages of from 0.1 to 10 mg./kg. of body weight daily.

The anti-anginal activity was first established by measuring the increase in coronary sinus partial pressure of oxygen ($pO_2$) according to the method of Schoepke et al., *Pharmacologist* 8: 204 (1966).

In addition to their cardiovascular activity, the compounds also exhibit central nervous system depressant activity at dosages of from 0.1 to 10 mg./kg. of body weight in test animals.

Generally speaking, the compounds of this invention are prepared by reacting the corresonding adenosine-5'-carboxylic acid ester with chloroacetaldehyde. The amides can be prepared by converting 2',3'-isopropylidene adenosine-5'-carboxylic acid (prepapred from 2',3'-isopropylidene adenosine according to the method described by Harmon et al., *CHEM. IND.* 1969, 1141) to the corresponding acid chloride, and reacting the acid chloride with an appropriate amine of the formula $R_1R_2NH$, followed by hydrolytic cleavage of the isopropylidene group, according to the following reaction scheme:

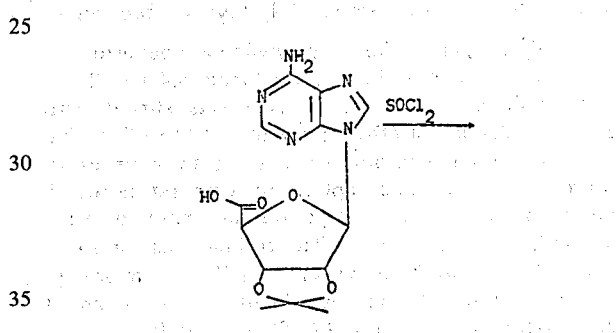

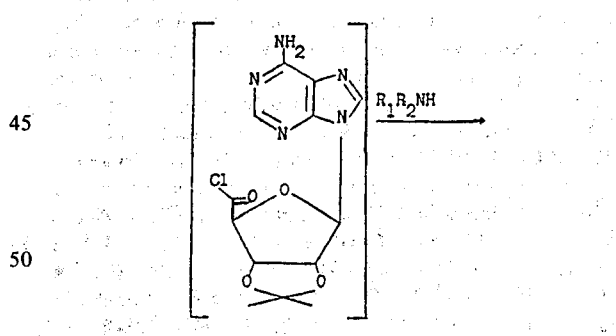

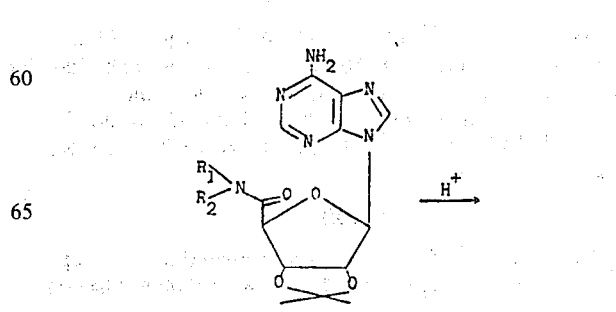

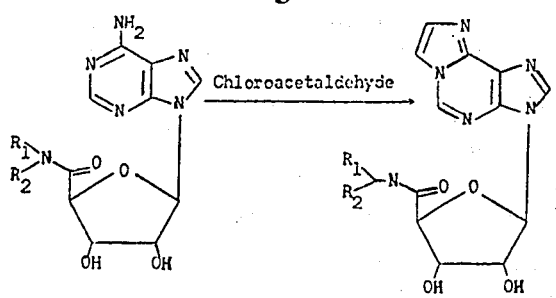

The following examples further illustrate this invention:

EXAMPLE 1

Preparation of Adenosine-5'-(N-ethyl) Carboxamide

Freshly prepared 2',3'-isopropylidene adenosine-5'-carboxylic acid chloride (prepared from 6.4 g. of 2',3'-isopropylidene-5'-carboxylic acid) was stirred with excess of dry liquid ethyl amine at −50° to −35°. The clear red-orange solution was allowed to warm up to room temperature and kept at this temperature for 15 hours. At the end of this period the excess of ethyl amine had evaporated off. The residue was triturated with cold aqueous $NaHCO_3$ solution. The white precipitate was filtered off and washed with a small amount of cold water to yield 3.1 g. (44.5%) of crude 2',3'-isopropylidene-5'[N-ethyl)-carboxamide] m.p. 225°–227°. $R_f$: 0.72 (silicagel) system: n-BuOH:$H_2O$:$N_4OH$ (86:14:5). This amide was mixed with 80 ml. of IN.HCl and kept at 65° for 45 minutes. The acidic solution was then cooled and basified with $NaHCO_3$. The mixture was then evaporated to dryness under reduced pressure and the residue recrystallized twice from absolute ethanol and finally from water. The white crystalline product was dried in vacuo for 2 days over $P_2O_5$ at 70°–78° to give 0.9 g. (32%) of adenosine-5'-[N-ethyl)-carboxamide] which melted slowly at 136°–172° and solidified again at 148°–150° and finally melted at 246°–247° (sharp). $[\alpha]_D^{26°}$ −163 (CO.92 in IN.HCl); $R_f$: 0.51 (silicagel). System: n-BuOH:$H_2O$:$N_4OH$ (86:14:05); NMR (deuterated DMSO) peaks (in ppm) at 5.6 (2'-OH, 3'-OH), 7.4 (6C-$NH_2$): 8.8 (CONH): 3.2 ($CH_2CH_3$).

Analysis Calcd. for $C_{12}H_{16}N_6O_4 \cdot H_2O$: C, 44.17; H,5.53; N, 25.76. Found: C, 44.33; H, 6.01; N, 25.78.

EXAMPLE 2

Adenosine-5'-(N-allyl)carboxamide, m.p. 223–24° dec., was prepared according to the method of Example 1, using allyl amine in place of ethyl amine.

Analysis Calcd. for $C_{13}H_{16}N_6O_4 \cdot H_2O$: C, 46.20; H, 5.36; N, 24.82; O, 23.62. Found: C, 46.26; H, 5.58; N, 24.92; O, 24.00.

EXAMPLE 3

Adenosine-5'-(N-cyclobutyl)carboxamide, m.p. 235–37° dec., was prepared according to the method of Example 1 using cyclobutylamine in place of ethylamine.

Analysis Calcd. for $C_{14}H_{18}N_6O_4$: C, 50.30; H, 5.42; N, 25.14. Found: C, 50.52; H, 5.56; N, 24.72.

EXAMPLE 4

1,$N^6$-Etheno Adenosine-5'-(N-allyl) Carboxamide

Chloroacetaldehyde (26.0 g; 0.1 mole of 30% aqueous solution) was added to a stirred suspension of adenosine-5'-(N-allyl) carboxamide (3.3 g; 0.01 mole) in water (80 ml.) containing a few drops of acetic acid at 50°C. In a few minutes the solid dissolved. After 17 hours at 50°C., the reaction solution gave only one fluorescent spot on the TLC paper. The cloudy reaction mixture was evaporated under reduced pressure. The oily residue solidified on trituration with acetone-ether. The amorphous solid, so obtained, was taken up in a large volume of methanol and stirred with Rexyn-203 [OH]. The methanolic solution was concentrated. Recrystallization of the residue gave the pure product, m.p. 242°–244°.

Analysis Calcd. For $c_{15}H_{16}N_6O_4$: C, 52.32; H, 4.68; N, 24.41. Found: C, 52.71; H, 4.69; N,24.33.

EXAMPLE 5

1,$N^6$-Etheno adenosine-5'-(N-cyclobutyl) carboxamide, m.p. 261°–262°, was prepared according to the method of example 4 from adenosine-5'-(N-cyclobutyl) carboxamide and chloroacetaldehyde.

Analysis Calcd. For $C_{16}H_{18}N_6O_4$: C, 53.63; H, 5.06; N, 23.45. Found: C, 53.21; H, 5.18; N, 23.04.

EXAMPLE 6

1,$N^6$-Etheno adenosine-5'-(N-ethyl) carboxamide, m.p. 252°–254°, was prepared according to the method of Example 4 from adenosine-5'-(N-ethyl) carboxamide.

Analysis Calcd. for $C_{14}H_{16}N_6O_4$: C, 50.60; H, 4.85; N, 25.29. Found: C, 50.27; H, 4.85; N, 25.07.

EXAMPLE 7

Tablets containing 25 mg. of 1,$N^6$ Etheno adenosine-5'-(N-allyl) carboxamide and having the following composition are prepared according to methods well known in the art.

| | |
|---|---|
| 1,$N^6$-Etheno adenosine-5'-(N-allyl) carboxamide | 10 mg. |
| Starch | 10 mg. |
| Colloidal Silica | 3 mg. |
| Magnesium stearate | 2 mg. |

The compounds of this invention can be formulated into various pharmaceutical dosage forms such as tablets, capsules, pills and the like, for immediate or sustained release, by combining the active compound with a suitable pharmaceutically acceptable carrier or diluent according to methods well known in the art. Such dosage forms may additionally include excipients, binders, fillers, flavoring and sweetening agents and other therapeutically inert ingredients necessary in the formulation of the desired pharmaceutical preparation.

We claim:
1. A method of increasing coronary sinus partial pressure of oxygen in a patient in need of such treatment comprising administering an effective coronary sinus partial pressure of oxygen increasing amount of a compound of the formula

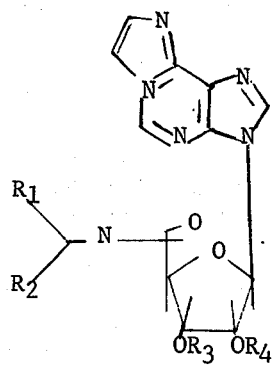

wherein $R_1$ and $R_2$ each are hydrogen, loweralkyl, a cycloalkyl of 3 to 6 carbon atoms, loweralkenyl or loweralkynyl and $R_3$ and $R_4$ each are hydrogen, acetyl, propionyl, butyryl, or $R_3$ and $R_4$ taken together form an isopropylidene or benzylidene moiety; or a pharmaceutically acceptable acid addition salt thereof, to said patient.

2. A method according to claim 1, wherein said compound is administered in a dosage of from 0.1 to 10.0 mg./kg. of body weight daily.

* * * * *